United States Patent [19]

MacNeil et al.

[11] Patent Number: 4,703,009
[45] Date of Patent: Oct. 27, 1987

[54] RDNA CLONING VECTOR PVE1, DELETION AND HYBRID MUTANTS AND RECOMBINANT DERIVATIVES THEREOF PRODUCTS AND PROCESSES

[75] Inventors: Tanya MacNeil, Westfield; Patrice H. Gibbons, Edison, both of N.J.

[73] Assignee: Merck & Co., Inc., Rahway, N.J.

[21] Appl. No.: 805,241

[22] Filed: Dec. 4, 1985

Related U.S. Application Data

[63] Continuation of Ser. No. 473,181, Mar. 8, 1983, abandoned.

[51] Int. Cl.$^4$ .................. C12N 15/00; C12N 1/00; C12N 1/20; C12P 19/34
[52] U.S. Cl. ......................... 435/172.3; 435/91; 435/243; 435/253; 435/68; 435/886; 435/906; 435/320; 935/29; 935/72; 935/73; 935/74; 935/75
[58] Field of Search ................... 435/886, 906, 68, 70, 435/91, 172.3, 253, 317, 243; 935/29, 72–75

[56] References Cited

U.S. PATENT DOCUMENTS 4,273,875 6/1981 Manis .................................. 435/317
4,460,693 7/1984 Toyama et al. ...................... 435/317

FOREIGN PATENT DOCUMENTS 0020251 12/1980 European Pat. Off. ......... 435/172.3
0035914  8/1981 European Pat. Off. ......... 435/172.3
0035914  9/1981 European Pat. Off. ......... 435/172.3
0038156 10/1981 European Pat. Off. ......... 435/172.3
 070522  1/1983 European Pat. Off. ............ 435/253
2031434  4/1980 United Kingdom ............. 435/172.3
2045253 10/1980 United Kingdom ............. 435/172.3
2045252 10/1980 United Kingdom ............. 435/172.3
2044773 10/1980 United Kingdom ............. 435/172.3
2043652 10/1980 United Kingdom ............. 435/172.3
2045251 10/1980 United Kingdom ............. 435/172.3
2045254 10/1980 United Kingdom ............. 435/172.3
2046272 11/1980 United Kingdom ............. 435/172.3

OTHER PUBLICATIONS

American Type Culture Collection Catalogue of Strains I, 13th Edition, 1978, p. 174.
Akagawa et al: Chem. Abstr. 91:71559d (1979) of J. Antibiot. 32(6), 610 (1979).
Bibb, M. J., Schottel, J. L., Cohen, S. N., 1980, Nature 284:526–531.
Thompson, C. J., Ward, J. and Hopwood, D., 1982, J. Bacteriol, 151:668–677.
Bibb, M. J., Ward, J. M., Kieser, T., Cohen, S. N. and Hopwood, D., 1981, Mol. Gen. Genet., 184:230–240.
Thompson, C. J., Ward, J. M. and Hopwood, D. A., 1980, Nature 286:525–527.

(List continued on next page.)

Primary Examiner—James Martinell
Attorney, Agent, or Firm—Robert J. North; Raymond M. Speer; Hesna J. Pfeiffer

[57] ABSTRACT

Novel plasmid pVE1, deletion mutants thereof, recombinant derivatives thereof, which is the same as the genome or nucleic acid of such plasmids and derivatives of such genome, which are useful as recombinant DNA cloning vectors into host organisms, such as bacteria, for example, Streptomyces avermitilis; portions of such plasmid genome are additionally useful as adjuncts in recombinant DNA cloning procedures, for examples: 1. to permit the maintenance of cloned DNA in the host, either in an integrated state or as an autonomous element; 2. to serve as promoters for increasing expression of endogenous or foreign genes wherein said promoters are ligated to such genes or otherwise serve as promoters; and 3. to serve as regulatory elements for achieving control over endogenous and foreign gene expression; as cloning vectors, pVE1 its deletion mutants, and other derivatives serve for the amplification and transfer of DNA sequences (genes) coding for useful functions, such modified cloning vectors are introduced into the recipient organism by conjugation or transformation; wherein the hybrid DNA functions in an integrated mode and/or in a plasmid mode.

25 Claims, 8 Drawing Figures

OTHER PUBLICATIONS

Kieser, T., Hopwood, D. A., Wright, H. M. and Thompson, C. J., 1982, pIJ101, Molec. Gen. Genet. 185:223–238.

Pernodet, J. and Guerineau, M., 1981, Mol. Gen. Genet. 182:53–59.

Okanishi, M., Suzuki, K. and Umezawa, H., 1974, J. Gen. Microbiol. 80:389–400.

Bibb, M. J., Ward, J. M. and Hopwood, D. A., 1978, Nature, 274:398–400.

Isogai, T., Takahashi, H. and Saito, H., 1981, J. Gen. Appl. Microbiol. 27:373–379.

Suarez, J. E. and Chater, K. F., 1980, Nature, 286:527–529.

Chater, K. F., Hopwood, D. A., Kieser, T. and Thompson, C. J., 1982, Curr. Top. Microbiol. Immunol 96:69–95.

Schottel, J. L., Bibb, M. J. and Cohen, S. N., 1981, J. Bacteriol. 146:360–368.

Chung, S.-T., 1982, Gene 17:239–246.

Manis, J. J. and Highlander, S. K., 1982, Gene 18:13–20.

Kirby, R., Lewis, E. and Botha, C., 1982, Microbiol. Let. 13:79–82.

Omura, S., Ikeda, H. and Tanaka, H., 1981, J. Antibiotics 34:478–482.

Yi-Guang, W., Davies, J. and Hutchinson, C. R., 1982, J. Antibiotics 35:335–342.

Toyama, H., Hayashi, E., Nojiri, C., Katsumata, K., Miyata, A. and Yamada, Y., 1982, J. Antibiotics 35:369–373.

Okanishi, M., Manome, T. and Umezawa, H., 1980, J. Antibiotics 33:88–91.

Hayakawa, T., Otake, N., Yonehara, H., Tanaka, T. and Sakaguchi, K., 1979, J. Antibiotics 32:1348–1350.

pVE28: A DELETED VARIANT OF pVE1

REGIONS OF pVE1
NOT ESSENTIAL FOR PLASMID MAINTENANCE

OPEN AREAS ARE SEGMENTS WHICH CAN BE DELETED
WITHOUT AFFECTING PLASMID STABILITY

INSERTION ANALYSIS OF pVE1 u INDICATES INSERTION HERE MAKES PLASMID UNSTABLE
+ = PLASMID WITH INSERTION HERE IS STILL SELF-TRANSMISSIBLE
− = PLASMID WITH INSERTION HERE IS NO LONGER SELF-TRANSMISSIBLE

RDNA CLONING VECTOR PVE1, DELETION AND HYBRID MUTANTS AND RECOMBINANT DERIVATIVES THEREOF PRODUCTS AND PROCESSES

REFERENCES TO RELATED APPLICATIONS

This is a continuation of Ser. No. 473,181, filed Mar. 8, 1983, now abandoned.

BACKGROUND OF THE INVENTION

1. Field of the Invention

This invention relates to the incorporation of nucleic acid into cellular systems, to vectors effecting such incorporation, and to microorganisms comprising such vectors.

More specifically, this invention relates to the novel plasmid pVE1, per se; its genome, or genetic component (DNA), entire and as fragments; and its derivatives (deletion and hybrid variants thereof) which are useful as cloning vectors into organisms, such as bacteria, including in particular plasmid pVE1 host strains, for example, *Streptomyces avermitilis* MA4990, *S. lividans*, or the like. The resultant modified cells are novel and have utility either as a means of producing the foreign nucleic acid and/or its products through replication of the cells, or through the imparting of valuable properties to the cells by virtue of the presence of the foreign nucleic acid therein.

2. Brief Description of the Prior Art

The use of plasmids as cloning vectors is a well established procedure. However, the application of these techniques to Streptomyces is relatively new.

DNA cloning with plasmid vectors and Streptomyces has been done primarily in *S. lividans* and *S. coelicolor* A3(2). SCP2, a low copy number plasmid of 31 kb, was used to clone the gene for methylenomycin resistance [(1) Bibb, M. J., Schottel, J. L., Cohen, S. N., 1980. "A DNA cloning system for interspecies gene transfer in antibiotic producing Streptomyces," *Nature* 284: 526–531]; and to clone *S. coelicolor* genes which complemented auxotrophic mutations [(2) Thompson, C. J., Ward, J. and Hopwood, D., 1982, "Cloning of antibiotic resistance and nutritional genes in Streptomyces," *J. Bacteriol*, 151: 668–677]. Genes encoding resistance to neomycin, thiostrepton, and viomycin have been cloned into the SLP1 plasmid family, a group of low copy number plasmids derived from the *S. coelicolor* A3(2) chromosome [(3) Bibb, M. J., Ward, J. M., Kieser, T., Cohen, S. N. and Hopwood, D., 1981, "Excision of chromosomal DNA sequences for *Streptomyces coelicolor* forms a novel family of plasmids detectable in *Streptromyces lividans*," *Mol. Gen. Genet.*, 184: 230–240; (4) Thompson, C. J, Ward, J. M. and Hopwood, D. A., 1980, "DNA cloning in Streptomyces: Resistance genes from antibiotic producing species," *Nature* 286: 525–527; Thompson, C. J., Ward, J. M. and Hopwood, D. A., 1982, supra]. The genes for neomycin, thiostrepton and viomycin resistance (aph, tsr and vph, respectively) were also cloned into a high copy number, broad host range plasmid, pIJ101, obtained from *S. lividans* ISP 5434 [(5) Kieser, T., Hopwood, D. A., Wright, H. M. and Thompson, C. J., 1982, pIJ101, "A multi-copy broad host range Streptomyces plasmid: Functional analysis and development of DNA cloning vectors," *Molec. Gen. Genet.* 185: 223–238]. This plasmid has also been isolated from *S. coelicolor* ATCC 10147 [(6) Pernodet, J. and Guerineau, M., 1981, "Isolation and physical characterization of Streptomyces plasmids," *Mol. Gen. Genet.* 182: 53–59]. SCP2, SLP1 and pIJ101 are all self-transmissible plasmids. When a strain containing one of these plasmids is plated on a plasmid-free strain, a small zone of growth inhibition, known as a pock, is formed in the lawn around the plasmid-containing strain. Plasmid DNA is introduced into Streptomyces by polyethylene glycol (PEG) mediated transformation of protoplasts [(7) Okanishi, M., Suzuki, K. and Umezawa, H., 1974, "Formation and reversion of Streptomyces protoplasts: Cultural conditions and morphological study," *J. Gen. Microbiol.* 80: 389–400; (8) Bibb, M. J., Ward, J. M. and Hopwood, D. A., 1978, "Transformation of plasmid DNA into Streptomyces at high frequency," *Nature*, 274: 398–400].

Bacteriophage have also been used as cloning vectors in Streptomyces [(9) Isogai, T., Takahashi, H. and Saito, H., 1981, "Actinophage R4 as a DNA cloning vector in Streptomyces," *J. Gen. Appl. Microbiol.* 27: 373–379; (10) Suarez, J. E. and Chater, K. F., 1980, "DNA cloning in Streptomyces: A bifunctional replicon comprising pBR322 inserted into a Streptomyces phage," *Nature*, 286: 527–529]. A review of methods and currrent progress in Streptomyces cloning can be found in (11) Chater, K. F., Hopwood, D. A., Kieser, T. and Thompson, C. J., 1982, "Gene cloning in Streptomyces," *Curr. Top. Microbiol. Immunol.* 96: 69–95.

Hybrid replicons which function in *E. coli* and Streptomyces have been constructed by linking the *E coli* plasmid pBR322 to Streptomyces phage φC31 (Suarez, J. E. and Chater, K. F., 1980, supra), to a derivative of SLP1 (Chater, K. F., Hopwood, D. A., Kieser, T. and Thompson, C. J., 1982, supra), and to a *Streptomyces espinosus* plasmid pUC6 [(12) European Patent Application 0035914A2; No. 81301009.7; published Sept. 16. 1981] and also by joining pACYC177 or pACYC184 to a derivative of SLP1 [(13) Schottel, J. L., Bibb, M. J. and Cohen, S. N., 1981," Cloning and expression in *Streptomyces lividans* of antibiotic resistance genes derived from *Escherichia coli*," *J. Bacteriol.* 146: 360–368].

A great variety of plasmids have been observed in many different Streptomyces and may have the potential to be developed into cloning vectors. For example, see the following:

(14) Chung, S. T., 1982, "Isolation and characterization of *Streptomyces fradiae* plasmids which are prophage of the actinophage φSF1," *Gene* 17: 239–246.

(15) Manis, J. J. and Highlander, S. K., 1982, "Partial characterization of a small, multi-copy plasmid from *Streptomyces espinosus* and the derivation of a high copy-number deletion mutant," *Gene* 18: 13–20.

(16) Kirby, R., Lewis, E. and Botha, C., 1982," A survey of Streptomyces species for covalently closed circular (ccc) DNA using a variety of methods, "FEMS *Microbiol.* Let. 13: 79–82.

(17) Omura, S., Ikeda, H. and Tanaka, H., 1981," Extraction and characterization of plasmids from macrolide antibiotic-producing Streptomycetes," *J. Antibiotics* 34: 478–481.

(18) Yi-Guang, W., Davies, J. and Hutchinson, C. R., 1982, "Plasmid DNA in the erythromycin producing microorganism *Streptomyces erythreus* NRRL 2338," *J. Antibiotics* 35: 335–342.

(19) Toyama, H., Hayashi, E., Nojiri, C., Katsumata, K., Miyata, A. and Yamada, Y., 1982, "Isolation and characterization of small plasmids from Streptomyces," *J. Antibiotics.* 35 369–373.

(20) Okanishi, M., Manome, T. and Umezawa, H., 1980, "Isolation and charaterization of plasmid DNAs in actinomycetes," *J. Antibiotics* 33: 88–91.

(21) Hayakawa, T., Otake, N., Yonehara, H., Tanaka, T. and Sakaguchi, K., 1979, "Isolation and characterization of plasmids from Streptomyces," *J. Antibiotics* 32: 1348–1350.

(22) UK Patent Application G.B. 2045253A; No. 8007080; published Oct. 29, 1980 (pUC1).

(23) UK Patent Application G.B. 2045252A; No. 8007079; published Oct. 29, 1980 (pUC2).

(24) UK Patent Application G.B. 2044773A; No. 8007077; published Oct. 22, 1980 (pUC3).

(25) UK Patent application G.B. 2043652A; No. 8007158; published Oct. 8, 1980 (pUC6).

(26) UK Patent Application G.B. 2046272A; No. 8011000; published Nov. 12, 1980 (pUC7).

(27) UK Patent Application G.B. 2045251A; No. 8007078; published Oct. 22, 1980 (pUC8).

(28) UK Patent Application G.B. 2045254A; No. 8007081; published Oct. 29, 1980 (pUC9).

(29) European Patent Application 0038156A2; No. 81301482.6; published Oct. 21, 1981 (pUC10).

(30) European Patent Application 0035914A2; No. 81301009.7; published Sept. 16, 1981 (pUC1012 and pUC1013).

(31) European Patent Application 0020251A2; No. 80400722.7; published Dec. 10, 1980 (hepatitis B plasmid vector).

(32) UK Patent Application G.B. 2031434A; No. 7928156; published Apr. 23, 1980 (Chimeric proteins to make hepatitis B antigen).

DETAILED DESCRIPTION OF THE INVENTION AND PREFERRED EMBODIMENTS

Plasmid pVE1 is a unique plasmid with a unique set of physical and genetic properties which may offer specific advantages over other cloning vectors in a particular situation. Its unique restriction map permits use of restriction enzymes or combinations of enzymes which may be appropriate only for pVE1. Both multicopy and single-copy plasmid vectors have been used for cloning in Streptomyces. In some experiments it is desirable to have the cloned gene present in many copies per cell, for example, in order to maximize the amount of the cloned gene product. A high copy number cloning vector is one approach to this goal. pVE1 is such a high copy number plasmid. pVE1 is also a self-transmissible plasmid. This offers the advantage of an alternative method of introducing the plasmid into a host. For example, if a Streptomyces host cannot be transformed due to difficulty in making or regenerating protoplasts, it is possible to first transform the pVE1 derivative into protoplasts of *S. lividans* and then mate this strain with the Streptomyces host of interest. Plasmids have varying host ranges which may be narrow or very broad among Streptomyces species. pVE1 can be maintained in *S. venezulae, S. lividans* and *S. avermitilis*, and may be a potential cloning vector for additional Streptomyces species.

The plasmid nucleic acid is a circular double-stranded DNA molecule 11.0 kilobasepairs in length. FIG. 1 is a map indicating the locations of the restriction endonuclease cleavage sites of the plasmid DNA. The locations are given as the distance of the site in kilobasepairs from the end of the plasmid DNA formed by cleavage with the Hind III restriction enzyme. The map shows all sites for the enzymes Hind III, Eco RI, Eco RV, Bam HI, Pvu I, Bcl I, Bgl II, Cla I, Pst I, Sph I, Pvu II, Stu I, Not I, and Nru I which could be determined by agarose and polyacrylamide gel electrophoresis and ethidium bromide staining of fragments of 0.1 kilobasepairs and larger. The following enzymes fail to cleave the DNA: Hpa I, Kpn I, Nco I, Nde I, Pae R7, and Xho I. Certain plasmid deletion variants and hybrid phage derivatives are similarly described below. Plasmid pVE1 is described in greater detail below; wherein unambiguous characterizing information relating to isolation, maintenance, propagation of the plasmid as defined, inter alia, by size and restriction mapping is given. Further, as described below, microorganisms containing pVE1, and representative pVE1 derivatives are deposited in a culture collection authorized under the Budapest Treaty on the International Recognition of the Deposit of Microorganisms for the Purposes of Patent Procedure (see Table I).

As disclosed herein, plasmid pVE1 and its recombinant derivatives or portions thereof, have utility, inter alia, as cloning vehicles in recombinant DNA procedures.

pVE1 is a unique plasmid which can be used in a variety of ways as a cloning vector in Streptomyces. Several properties of the plasmid make it a useful cloning vehicle. A significant feature is the high copy number and small size of the plasmid. This makes isolation of large quantities of plasmid DNA feasible and simple. The high copy number of the plasmid means that whatever gene is cloned into the plasmid will also be present in many copies per cell. This affords a means for producing a large amount of the cloned gene product or metabolite made by the gene product. Another advantageous feature of pVE1 is the large region of the plasmid defined by the 7 kb deletion in pVE28 which appears to be nonessential for plasmid maintenance. This offers a potentially large stretch of DNA with a variety of restriction sites into which foreign DNA can be cloned. Thus, the Bam HI, Eco RI, Bgl II and Bcl I sites in this region have been used for cloning.

The methods used for cloning illustrated in the Examples herein involve construction of the cointegrate plasmids pVE3 and pVE4 as well as direct cloning of the tsr gene into several sites in pVE1. These methods and additional useful cloning techniques are amply described in the previously cited manuals. (Davis, R. W., Botstein, D., and Roth, J. R., 1980, supra; Maniatis, T., Fritsch, E. F., and Sambrook, J., 1982, supra).

The cloning procedure can be modified in a variety of ways. First, it is possible to use any of the derivatives constructed from pVE1 described herein. It is also possible to construct new vectors based on the pVE1 replicon by insertion of other selectable markers, for example resistance to neomycin (Thompson, C. J., Ward, J. M. and Hopwood, D. A., 1980, supra). Additional useful vectors may be constructed by deletions formed in vitro. pVE1 may be digested with restriction enzymes, the fragments or subset of fragments ligated and transformed into Streptomyces to obtain shortened plasmids.

Foreign DNA can be inserted into pVE1 by a variety of methods. Both DNA molecules can be cut by the same restriction enzymes and these molecules with homologous ends can be ligated together. Vector and insert DNA may be digested with different enzymes which generate the same single strand extension allowing efficient pairing and ligation. Vector and insert DNA may be cleaved with completely dissimilar restriction enzymes, the cleaved DNA treated with S1 nuclease or DNA polymerase to remove the single stranded protruding end or to synthesize the complementary strand of such an end, respectively. This yields blunt-ended DNA molecules which can be ligated together Another modification which may be used is the addition of short homopolymeric extensions by terminal deoxynucleotidyltransferase to the 3' ends of linear vector and foreign DNA. Annealing of vector and insert DNA with complementary homopolymer tails is followed by transformation into the bacterial host without prior ligation.

pVE1 and its derivatives may be used to clone Streptomyces genes of primary metabolism, for example, genes involved in the biosynthesis of amino acids, vitamins, purines and pyrimidines. To detect such recombinant plasmids, the ligated DNA is transformed into protoplasts of a particular auxotrophic strain. Transformants are initially selected by the phenotype conferred by the vector, e.g. Thio$^r$. These plasmid-containing strains are tested for growth in the absence of the nutrient required by the auxotroph. Only strains which acquired the complementing wild type gene in the recombinant plasmid are capable of growth.

pVE1 can be used to clone genes of secondary metabolism, such as genes involved in the production of antibiotics. Recombinant plasmids are transformed into a mutant blocked in the production of the metabolite. Transformants are selected by the plasmid phenotype. One then assays these transformants to identify those with a plasmid that now complements the mutation that blocks secondary metabolite production. Since mutations and genes of secondary metabolism usually do not affect growth, this assay is somewhat more complicated and depends on the specific metabolite involved. If the product is an antibiotic, transformed colonies are overlain with a lawn of an antibiotic sensitive organism. Colonies containing the cloned complementing gene would produce the antibiotic and be surrounded by a zone of growth inhibition of this sensitive test organism. If no simple biological assay exists for the product, it is possible to use physical or chemical methods of detection. For example, production of the antihelminthic compounds, the avermectins, by S. avermitilis (Burg, R. W. et al., 1979, Antimicrobial Agents and Chemotherapy, 15, 361–367) is routinely assayed by high pressure liquid chromatography.

Recombinant plasmids containing cloned genes have many experimental uses. With such a rich source of the purified gene, it is possible to perform a detailed genetic and physical analysis of the gene to identify regulatory regions and the coding region for the structural gene. The DNA sequence of the gene or portions of it can be determined. If a gene of interest has been cloned into a vector which is a bifunctional replicon, such as pVE3 or pVE4 which replicate in both E. coli and Streptomyces, many additional experiments are then possible. Because of the thorough genetic characterization of E. coli, vectors such as pVE3 and pVE4 enable one to perform a variety of in vivo genetic manipulations in E. coli that are not yet possible in Streptomyces.

Recombinant plasmids containing cloned genes can be reintroduced into the wild type host organism to determine the effect of high copy number of a gene in the biosynthetic pathway of the secondary metabolite. For example, if the rate limiting step in a pathway has been cloned, supplying this gene in many copies per cell may greatly increase the yield of the metabolite. If several or all of the genes of a particular metabolic pathway have been cloned, it may be posssible to construct in vitro a single plasmid containing the complete pathway. This would allow an increase in the gene dosage of all steps involved and perhaps thereby increase the productivity of the strain.

The cloned gene can be manipulated in vitro in a variety of ways to increase the level of its expression. In vitro mutagenesis of the DNA presumably yields mutants with both positive and negative effects on the expression of the gene. Control sequences, such as high level promotors, can be introduced at the appropriate site next to the cloned gene to increase its level of expression. The effect of all alterations is monitored by reintroducing the altered cloned gene into the host Streptomyces.

pVE1 replicons may be used to clone DNA from non-Streptomyces sources into Streptomyces to obtain production of a foreign protein. For this type of manipulation it is necessary to insert the foreign gene into a region of the vector which is already transcribed and translated under the control of Streptomyces regulatory sequences. For example, it is possible to use the aph gene for neomycin resistance cloned from S. fradiae into pIJ2 (Thompson, A. J., Ward, J. N. and Hopwood, D. A., 1980, supra). This gene is transcribed and translated at high levels (J. Davies, presented at the Fourth International Symposium on Genetics of Industrial Microorganisms, June 1982). If a foreign gene is inserted into aph, it may be possible to make high levels of a fusion protein between the aph protein and the foreign protein.

The plasmid host Streptomyces avermitilis produces the complex of chemically related agents called avermectin, which exhibits extraordinarily potent anthelmintic activity (see R. W. Burg et al; 15 Antimicrobial Agents and Chemotherapy, pp. 361–367 (1979)). The plasmid can be used for the identification, isolation, and study of the genes and gene products involved in the synthesis and regulation of the synthesis of these important compounds by genetic complementation of mutations in these genes (e.g., see Example 1, Section G.).

Certain hybrid derivatives of plasmid pVE1 are useful in other ways. These hybrids, whose construction and properties are described in Example 1, Section D, allow pVE1 vector derivatives to replicate as plasmids in Escherichia coli. These hybrid plasmid-plasmid vectors can be transferred between species by transformation. This property is extremely useful, since it allows the use of genetic techniques which have been developed for Escherichia coli. For example, genes from Streptomyces species may be found capable of complementing mutations in E. coli. Mutations can be introduced into the Streptomyces gene in E. coli, for instance, by the use of transposon mutagenesis; or mutations capable of being suppressed by nonsense suppressors (translational stop codons) might be isolated. The latter mutated genes can be transferred back into Streptomyces and used to isolate mutations capable of suppressing translational stop codons in Streptomyces. Such suppressor mutations are very useful in genetic studies of such an organism.

TABLE I

| Microorganism Deposit | | |
|---|---|---|
| Strain Number[a] | Resident Vector | Accession Number[b] |
| MA4192 | pVE1 | ATCC 14585 |
| MB4597 | pVE3 | ATCC 39298 |

TABLE I-continued

| Strain Number[a] | Microorganism Deposit Resident Vector | Accession Number[b] |
|---|---|---|
| MA5898 | pVE3 | ATCC 39301 |
| MA5904 | pVE28 | ATCC 39299 |
| MA5905 | pVE30 | ATCC 39300 |
| MA5894 | pVE9 | |
| MA5895 | pVE11 | |
| MA5896 | pVE13 | |
| MA5897 | pVE17 | |
| MA5899 | pVE19 | |
| MA5900 | pVE21 | |
| MA5901 | pVE23 | |
| MA5902 | pVE24 | |
| MA5903 | pVE26 | |
| MA5906 | pVE33 | |
| MA5907 | pVE35 | |
| MA5908 | pVE37 | |
| MA5909 | pVE39 | |

[a]Strain designations are those of the culture collection of MERCK and CO., Inc., Rahway, New Jersey. MA4192 is a derivative of *Streptomyces venezuelae*, and MA5894–MA5909 are derivatives of *Streptomyces lividans*. MB4597 is a derivative of *Escherichia coli* K-12 RR1. *E. coli* K-12 RR1 is described by F. Bolivar, R. L. Rodriquez, M. C. Betlach, and H. W. Boyer: 2 Gene, pp. 75–93 (1977).

[b]Cultures of each strain have been placed on permanent deposit with the American Type Culture Collection (ATCC), 12301 Parklawn Drive, Rockville, Md., and were complete as of February 28, 1983; and were assigned the indicated accession numbers.

Restriction map of plasmid pVE1.

The locations are given as the distance of the site in kilobasepairs from the 0/11 kb point of reference, which is the single Hind III site. The map shows all sites for the enzymes which could be determined by agarose and polyacrylamide gel electrophoresis and ethidium bromide staining of fragments of 0.1 kilobasepairs and larger.

FIG. 2

Restriction enzymes which cut pVE1 once.

This figure conveniently illustrates the circular pVE1 plasmid and the location of the unique restriction sites therein.

Figure 3:
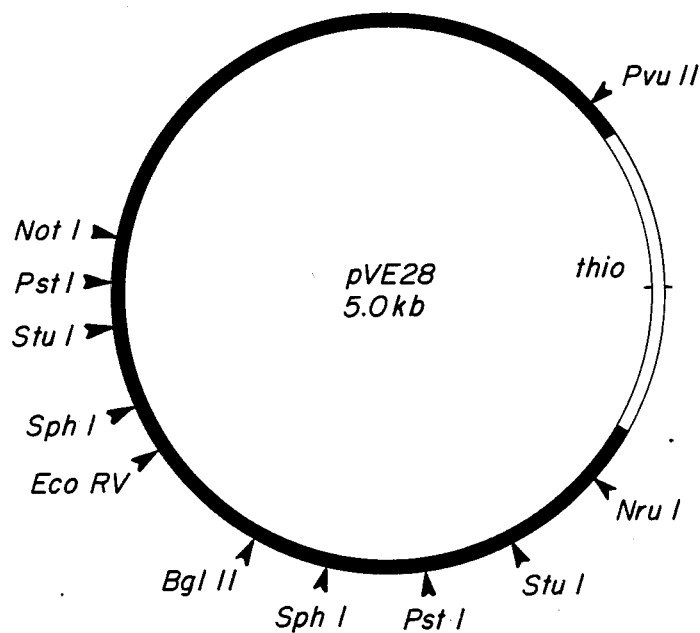
Figure 4:
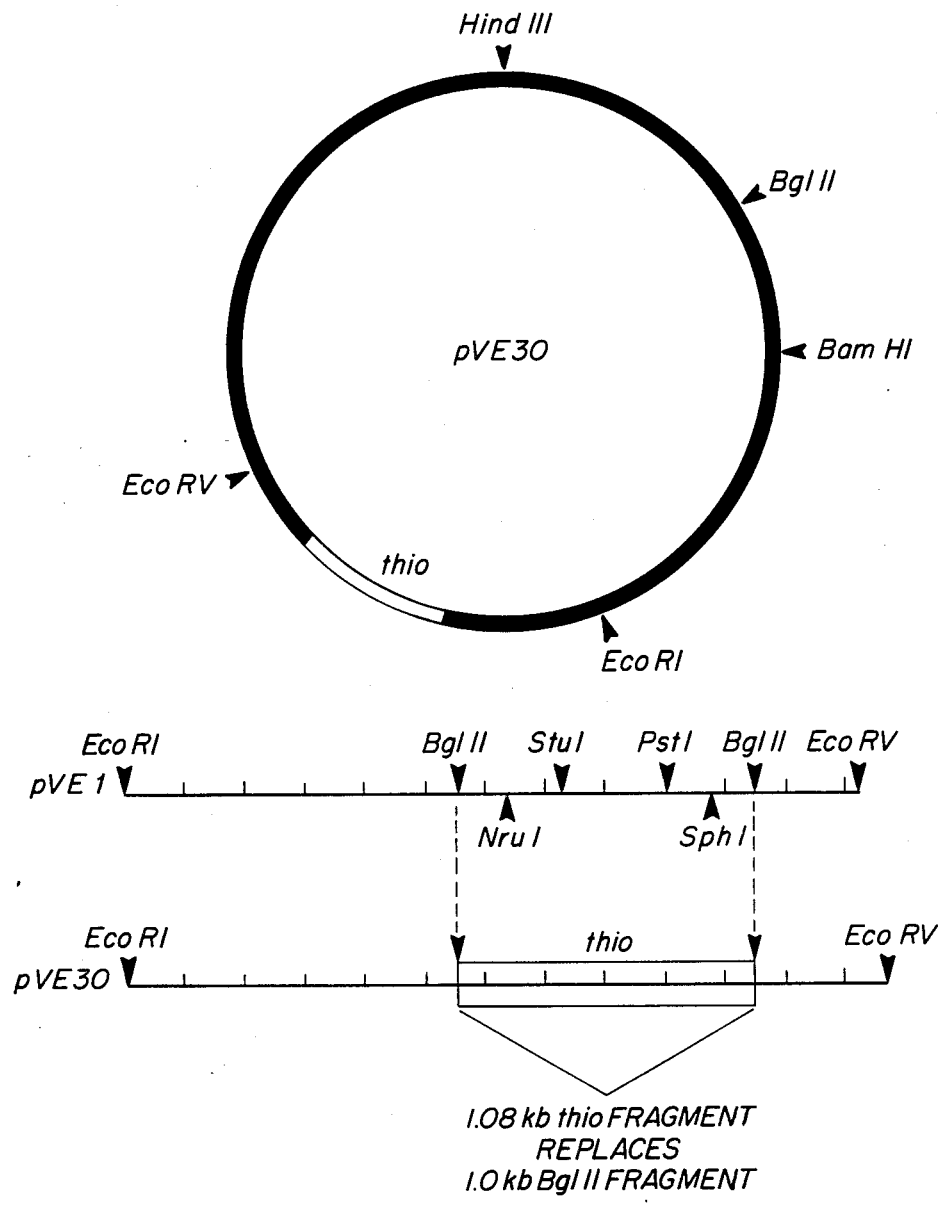
Figure 5:
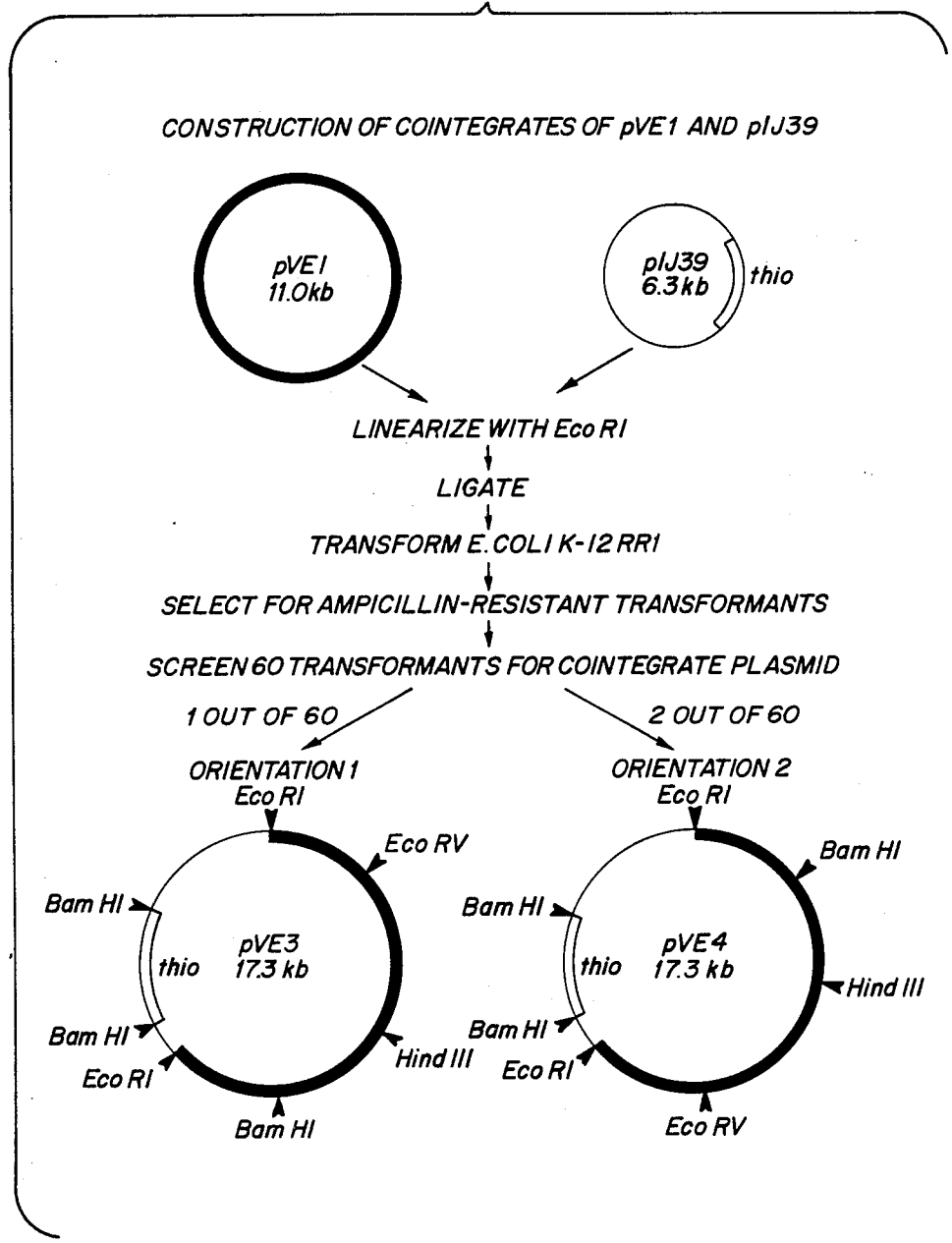

FIGS. 3 and 4 pVE28 and pVE30: deleted variants of pVE1.

These figures illustrate the two deletion variants of pVE1 :pVE28 and pVE30, respectively. .

pVE28 and pVE30 are plasmids obtained from the experiment in which the Bcl I tsr fragment was cloned into pVE1 partially digested with Bgl II.

Insertion of the tsr gene in pVE30 was accompanied by a deletion of the DNA between the two Bgl II sites at 6.15 and 7.15 kb on pVE1. pVE30 contains only a single Bgl II site in contrast to pVE1 which contains three Bgl II sites.

pVE28 is a much smaller plasmid. Insertion of the tsr fragment at the Bgl II 6.15 kb site was accompanied by a spontaneous deletion of 7.2 kb. pVE28 has a single Bgl II site suitable for cloning.

FIG. 5

Construction of cointegrates of pVE1 and pIJ39.

This figure demonstrates the method used to prepare the cointegrate of the two indicated plasmids.

FIG. 6

This figure depicts a restriction map of Bam HI fragments which encode resistance to thiostrepton (tsr) and neomycin (aph).

FIG. 7

Regions of pVE1 not essential for plasmid maintenance.

As the caption suggests, this figure depicts segments which can be deleted without affecting plasmid stability.

FIG. 8

Insertion analysis of pVE1.

This figure demonstrates those sites on the plasmid where insertions affect stability and self-transmiossibility.

The invention in several of its embodiments is representatively disclosed in this section in the format of "Examples". It is to be understood that this format is merely chosen as a convenient form of disclosure, without imposing any limitation upon the invention as hereinabove disclosed.

EXAMPLE 1

Isolation, Construction, Maintenance, and Propagation of pVE1 Vectors

The plasmid DNA was isolated and handled by procedures differing little from those established by work on other plasmids used as cloning vectors. A good procedures manual is R. W. Davis, D. Botstein, and J. R. Roth, "A Manual for Genetic Engineering: Advanced Bacterial Genetics," Cold Spring Harbor Laboratory, Cold Spring Harbor, New York (1980). The specific procedures used in this work are described herein, unless they are identical to those given in the above mentioned manual. Results which serve to characterize the pVE1 vector and its derivatives and differentiate them from other cloning vectors are mentioned where appropriate.

A. Growth of Streptomyces venezuelae MA4192 (ATCC 14585) for Plasmid Isolation

A single colony was inoculated into 25 ml of YEME (3 g yeast extract, 5 g peptone, 3 g malt extract, 1 g glucose per liter) in a 250 ml baffled flask with 34% sucrose and 5 mM $MgCl_2$ (Bibb, M. J., Freeman, R. F. and Hopwood, D. A., 1977, *Molec. Gen. Genet.* 154: 155–166). The culture was grown for 2 days at 27° C. with shaking at 220 rpm. This culture was diluted into 500 ml of the same medium in a 2 l flask and grown as above for 2 more days. The mycelia were harvested by centrifugation for 15 minutes at 14,000×g and washed once with 0.85% saline.

Plasmid isolation: Procedure 1.

A modification of the method described by Bibb et al., 1977, supra was used. The mycelia were resuspended in 25 ml of TE buffer [0.01M Tris (hydroxymethyl) aminomethane (Tris) and 0.001M ethylenediamine tetraacetate (EDTA], pH 7.9, containing 34% sucrose. 5.0 ml of 0.25M EDTA, pH 7.9, was added followed by 2.5 ml of lysozyme (50 mg/ml in 0.01M Tris). The mixture was incubated for 20 min at 37° C., transferred to an ice bath and additions of 20 ml of TE buffer with 34% sucrose and 15 ml of 0.25M EDTA were made. Sodium dodecyl sulfate (SDS) dissolved in TE buffer was added to give a final concentration of 1% followed by sodium chloride to a final concentration of 1M. This mixture was incubated on ice for 2 h or overnight. The SDS precipitate was removed by centrifugation at 30,000 rpm in a Beckman 60 Ti rotor for 45 min at 4° C. Polyethylene glycol (PEG) with an average molecular weight of 6,000 was added to the supernatant to a final concentration of 10% and the mixture was incubated 2 h to overnight at 4° C. The DNA-PEG precipitate was harvested by centrifugation at 5,000×g for 15 min at 4° C. This pellet was used for CsCl density gradients.

Plasmid isolation: Procedure 2.

A modification of a method described by Holmes, D. S. and Quigley, M., 1981, *Anal. Biochem.* 70: 431–441, was used. The washed mycelia were resuspended in 20 mls of STET buffer (8% sucrose, 5% Triton X-100, 50 mM EDTA and 50 mM Tris, pH 8.0). 0.5 ml of lysozyme (50 mg/ml in 0.01M Tris) was added and the mixture incubated 30 min at 37° C. The mixture was transferred to a boiling water bath for 2.5 min. This was centrifuged at 30,000 rpm in a Beckman 60 Ti rotor, 45 min, at 4° C. An equal volume of isopropanol was added to the supernatant. The mixture was chilled at −20° C. for at least 1 h and then centrifuged at 12,000×g for 15 min at 4° C. The DNA-PEG pellet (from method 1) or DNA pellet from isopropanol precipitation was resuspended in 13 ml of 10×TE buffer. 15.6 G of CsCl was added followed by 0.5 ml of ethidium bromide (5 mg/ml in water). The gradients were centrifuged at 37,000 rpm in a Beckman 50 Ti rotor for approximately 48 h. The plasmid band was collected and repurified by another CsCl density gradient. Ethidium bromide was removed by three extractions with equal volumes of isoamyl alcohol. CsCl was removed by dialysis against three changes of 1,000 volumes of DNA buffer (10 mM Tris pH 7.9, 10 mM NaCl, 0.1 mM EDTA). The plasmid DNA was extracted once with an equal volume of equilibrated phenol and 3 times with diethyl ether. Plasmid DNA was concentrated by ethanol precipitation. 0.1 Volume of 3M sodium acetate, pH 6, and 3 volumes of 100% ethanol were added to the DNA. The mixture was chilled at least 2 h at −20° C. and then centrifuged at 15,000×g, 15 min, at 4° C. The DNA pellet was resuspended in 0.5 to 1.0 ml of DNA buffer and stored at 4° C. The yield of plasmid DNA from 500 ml of cells was from 300 to 600 μg (suggesting that the plasmid has a high copy number—greater than 50 copies per cell).

Plasmid Isolation: Procedure 3.

A procedure modified from Holmes, D. S. and Quigley, M., 1981, supra, was used which was designed to rapidly obtain a small quantity of plasmid DNA from a large number of small cultures. 20 Ml of YEME -34% sucrose-5 mM MgCl$_2$ in a 250 ml baffled flask were inoculated with a single colony of a strain to be tested for the presence of plasmid. This was grown for 3 to 5 days with shaking at 220 rpm at 27° C. Cells were harvested by centrifugation at 10,000×g for 10 min and washed once with 0.85% saline. The cell pellet may be stored frozen at this stage. The pellet was resuspended in approximately 0.8 ml of STET buffer. 0.05 Ml of lysozyme (50 mg/ml in TE) was added and the mixture incubated at 37° C. for 30 min and then in a boiling water bath for 90 sec. The lysate was centrifuged at 12,000×g for 15 min. 0.5 Ml of the supernatant was recovered, extracted once with equal volume of equilibrated phenol, and the nucleic acid precipitated with an equal volume of isopropanol. The pellet was resuspended in 100 μl of DNA buffer. This DNA was suitable for transformation into Streptomyces or *E. coli*. One to ten μl of this DNA could be cleaved with restriction enzymes, with 20 μg/ml ribonuclease A for 15 min at 37° C., and analyzed by agarose gel electrophoresis.

The plasmid miniprep procedure described immediately above was used to examine plasmid DNA from *S. lividans* carrying pIJ6 (a derivative of SLP1.2 with a copy number of 1 to 2 per cell), pIJ303 (a derivative of pIJ101 present in greater than 50 copies per cell), and pVE1 and its derivatives described herein. Samples of each were analyzed in parallel by agarose gel electrophoresis. Plasmids were visualized by photography of ethidium bromide stained gels under UV light. The amount of fluorescence of plasmid band is directly proportional to the amount of plasmid DNA. pIJ6 always appeared as a faintly fluorescing band due to its low copy number. pIJ303 always appeared as a heavy, brightly fluorescing band. pVE1 and its derivatives always formed a bright band, equal to or greater in intensity than that of pIJ303. This result suggested that pVE1 is a high copy number plasmid.

B. Restriction Analysis of plasmid DNA

Figure 1:
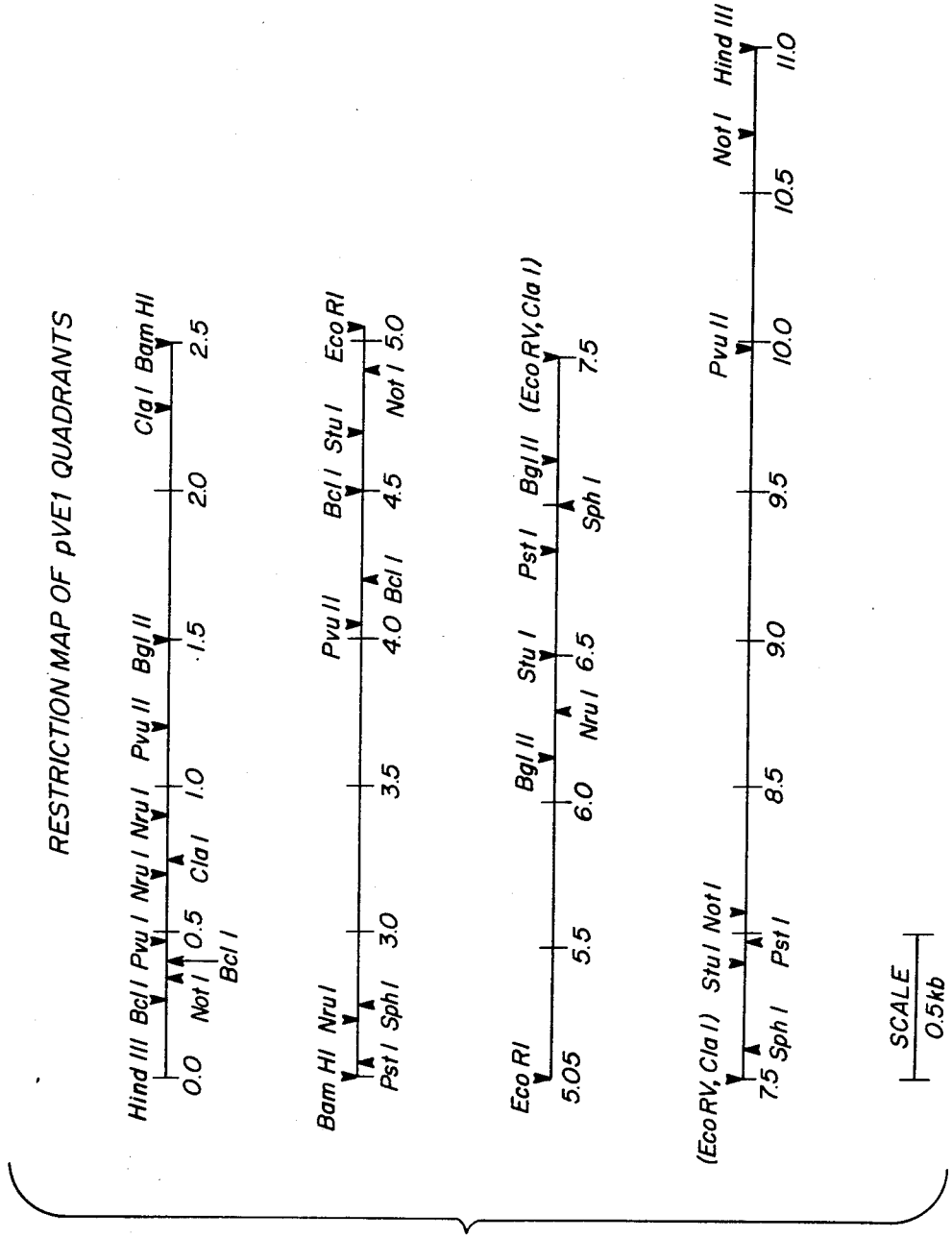
FIG. 1

Procedures for restriction analysis of DNA and agarose gel electrophoresis as well as other standard techniques of recombinant DNA technology are thoroughly described in two useful manuals: Davis, R. W., Botstein, D. and Roth, J. R., 1980, *Advanced Bacterial Genetics*, Cold Spring Harbor Laboratory, Cold Spring Harbor; and Maniatis, T., Fritsch, E. F. and Sambrook, J., 1982, *Molecular Cloning*, Cold Spring Harbor Laboratory, Cold Spring Harbor.

pVE1 DNA was cleaved by various restriction enzymes and combinations of enzymes. The DNA fragments were analyzed by electrophoresis in 0.8% agarose using 0.08M Tris-acetate—0.004M EDTA as buffer. The sizes of pVE1 fragments were determined by comparison with fragments of phage DNA of known molecular weight. pVE1 is a plasmid of 11.0 kb. It has single sites for the restriction enzymes Hind III (chosen as the 0/11.0 kb point of reference), Eco RI, Eco RV, Bam HI and Pvu I. It has multiple sites for Bcl I, Bgl II, Cla I, Not I, Nru I, Pst I, Pvu II, Sph I and Stu I. The restrictions sites for these enzymes were mapped and are shown in FIG. 1. The plasmid is cleaved many times by the enzymes Acc I, Ava I, Ava II, Bgl I, BstE II, Hae II, Hae III, HgiA I, Hinc II, Hph I, Mbo I, Mbo II, Nar I, Rsa I, Sal I, Sma I, Sst II, Tac I, Taq I and Tth 111 I. The following enzymes did not cleave pVE1: Hpa I, Kpn I, Nco I, Nde I, Pae R7 I and Xho I.

C. Transformation of Streptomyces by pVE1

(1) Protoplast formation.

Transformation was accomplished by PEG-mediated DNA uptake by protoplasts. The procedure used to make protoplasts was essentially that described in Thompson, C. J., Ward, J. M. and Hopwood, D. A., 1982, supra. 25 ml of YEME with 34% sucrose, 5 mM MgCl$_2$ and 0.5% glycine for *S. lividans* (1% glycine for *S. avermitilis*) was inoculated with 10$^8$ spores. This was incubated in a 250 ml baffled flask, two days, 27° C., with shaking at 220 rpm. Cells were harvested by centrifugation and washed once with 0.85% saline. The pellet was resuspended in approximately 10 ml of medium P containing 1 mg/ml lysozyme. Medium P (Okanishi, M., Suzuki, K. and Umezawa, H., 1974, supra) contains per liter 103 g sucrose, 0.25 g K , 2.03 g MgCl$_2$.6H$_2$O, 2 ml of a trace element solution. Trace element solution contains 40 mg ZnCl$_2$, 200 mg FeCl$_3$.6H$_2$O, 10 mg CuCl$_2$, 2H$_2$O, 10 mg MnCl$_2$.4H$_2$O, 10 mg Na$_2$B$_4$O$_7$.10H$_2$O and 10 mg (NH$_4$)$_6$Mo$_7$O$_{24}$. 4H$_2$O per liter. After 10 ml of sterile 0.5% KH$_2$PO$_4$, 10 ml of 2.5 M CaCl$_2$ and 40 ml of 250 mM TES, pH 7.2, (N-tris (hydroxymethyl) methyl-2-amino ethane-sulfonic acid) are added to form complete Medium P. For *S. avermitilis*, 40 ml of 250 mM MES, pH 6.0, (2-(N-morpholino) ethanesulfonic acid) was used instead of TES. Mycelia were incubated at 37° C. with lysozyme for 1 h. The suspension was filtered through 3 cc of glass wool and the filtrate centrifuged at 4,000×g for 5 min. The pellet was resuspended in 2 to 5 ml of Medium P. The protoplasts were used immediately or frozen at −70° C.

(2) Transformation procedure.

For transformations, 0.2 ml of protoplasts (approximately was $10^8$/ml) was diluted into 2.0 ml of medium P for washing, centrifuged at 3,000×g for 5 min and resuspended in the residual medium P. The DNA sample (0.01 to 1.0 μg in 10 μl DNA buffer) was mixed with the protoplasts. 0.5 ml of medium T was added and the mixture incubated for 1 min at room temperature. Medium T is similar to medium P except it contains different concentrations of sucrose (2.5%) and $CaCl_2$ (0.1M) and is buffered with 50 mM Tris-maleic acid (pH 8) and has 25% (wt/vol) PEG 1,000. The mixture was serially diluted in medium P and 0.1 ml aliquots plated on regeneration medium, R2YE for *S. lividans* and RM14 for *S. avermitilis*, so that protoplasts could regenerate cell walls. R2YE contains per liter 170 g sucrose, 3 g proline, and 0.25 g $K_2SO_4$, 10.1 g $MgCl_2.6H_2O$, 10 g glucose 0.1 g casamino acids, 2 ml of trace element solution, 3 g of yeast extract, and 15 g agar. Post-sterile additions of $CaCl_2$, $KH_2PO_4$ and TES were the same as those for medium P. RM14 is very similar to R2YE except it contains per liter 205 g sucrose, 20 g agar and an addition of 3 g oatmeal agar. The buffer added is MES as described for medium P.

(3) Detection of transformation.

Transformed protoplasts were diluted and plated on regeneration medium. Plates were incubated at 27° C. If the transforming DNA was a derivative of pVE1 with the tsr gene, the plates were overlayed at 24 h with 4 ml of regeneration medium which was only 0.7% agar containing suficient thiostrepton to give a final concentration of 50 μg/ml. After additional incubation of 3 to 4 days, Thio$^r$ colonies developed. Transformants were also detected by incubation of the original regeneration plates 4 to 7 days and replica plating these to similar medium containing 10 to 50 μg/ml thiostrepton. If the transforming DNA was a plasmid with no selectable marker, such as pVE1, or a derivative which was still self-transmissible, transformants were detected by pock formation. The original regeneration plates were incubated 4 to 7 days at 27° C. Small areas (1–2 mm) of inhibition of growth or inhibition of aerial mycelium formation, known as pocks, appeared in the regenerated lawn. This was due to the inhibition of mycelial development as the plasmid was transferred from the original transformed cell to surrounding plasmid-free cells.

Transformation of pVE1 into *S. lividans* by the method described above gave rise to pocks suggesting the self-transmissibility of this plasmid. Cells were purified by restreaking spores from the area of the pock to fresh medium. Single colonies were picked, grown and analyzed by the plasmid miniprep procedure described above. All colonies obtained from a pock contained pVE1. It was concluded that pVE1 was a self-transmissible plasmid.

D. Formation of Cointegrate Plasmid Between pVE1 and pIJ39.

This experiment demonstrates the feasibility of cloning foreign DNA into pVE1. pIJ39 contains a 1.9 kb Bam HI fragment containing the tsr (thiostrepton resistance) gene that was cloned from the plasmid pIJ6 (Thompson, C. J., Ward, J. M. and Hopwood, D. A., 1980, supra) into the Bam HI site of the ampicillin resistant *E. coli* plasmid pBR322 (Sutcliff, J. G., 1978, *Nucleic Acids Res.* 5: 2721–2728). pVE1 and pIJ39 were each separately linearized with Eco RI according to standard procedures. 2μg of linearized pVE1 were mixed with 15 μg (5 molar excess) of linearized pIJ39 at a final DNA concentration of 600 μg. This was treated in ligase buffer with T4 DNA ligase by standard procedures as described in Davis, R. W., Botstein, D. and Roth, J. R., 1980, supra. The ligation mixture was used to transform competent cells of *E. coli* K-12 RR1 (Bolivar, F., Rodriquez, R. L., Betlach, M. C. and Boyer, H. W., 1977, *Gene* 2: 75–93). RR1 was made competent by the method of Mandel, M. and Higa, A., 1970, *J. Mol. Biol.* 53: 159–162. Cells were grown in LB medium (10 g tryptone, 5 g yeast extract, 5 g NaCl per liter) to an $A_{600}=0.45$ and incubated on ice 20 min. Cells were pelleted and resuspended to one-half their original volume in 0.1M $CaCl_2$. After 20 min on ice, cells were again pelleted and resuspended to 0.1 of their original volume in 0.1 M $CaCl_2$. These competent cells were used for transformation or made 15% in glycerol and stored at −70° C.

For transformation, 0.2 ml of competent cells was mixed with 10% of the DNA from the ligation reactions between pVE1 and pIJ39. The mixture was incubated 2 min at 37° C. and then 1 h on ice. 3 ml of LB medium was added to the mixture in an 18×100 mm test tube and it was shaken at 220 rpm, 37° C. for 1.5 h. Aliquots were plated on LB agar plus 100 μg/ml ampicillin to select for cells transformed by pIJ39.

A plasmid miniprep analysis similar to that described above was performed on Amp$^r$ transformants to identify strains which contained the desired recombinant plasmid. Single colonies were inoculated into 5 ml of LB with ampicillin, grown overnight, pelleted by centrifugation and resuspended in 0.4 ml of STET buffer. 0.05 ml of lysozyme (50 mg/ml in TE) was added. The mixture was incubated in a boiling water bath 60 sec, centrifuged at 12,000×g for 12 min, and the supernatant precipitated with an equal volume of isopropanol. The nucleic acid was resuspended in 100 μl of DNA buffer and analyzed by restriction digestion and agarose gel electrophoresis.

Both possible recombinant plasmids were obtained. pVE3 and pVE4 are cointegrate plasmids between pIJ39 and pVE1 joined at their Eco RI sites in the 2 possible orientations. pVE3 and pVE4 were purified from 500 ml of cells by the Triton X-100 cleared lystate method of Clewell, D. B. and Helinski, D. R., 1969, *Proc. Natl. Acad. Sci. USA*, 62: 1159–1166.

Plasmid pVE$_3$ DNA was used to transform S. lividans protoplasts as described above. After 7 days of growth, regeneration plates showed pock formation. These plates were replica plated to R2YE medium containing 10 μg/ml thiostrepton and incubated 3 days at 27° C. The locations of Thio$^r$ colonies corresponded exactly to pocks in the original regeneration plate suggesting transformation by the cointegrate plasmid had occurred and that pVE3 was still self-transmissible. Ten Thio$^r$ colonies were purified and used to grow cultures for the plasmid miniprep procedure. Restriction analysis of the DNA obtained showed these colonies contained the plasmid pVE3.

These colonies were used in mating experiments with a streptomycin resistant derivative of *S. lividans*. All strains were grown for 2 days in 3 ml of YEME-34% sucrose-5 mM $MgCl_2$ in a 18×100 mm tube. R2YE agar plates or YD plates (4 g yeast extract, 10 g malt extract, 4 g dextrose and 15 g agar per liter, 10 mM CaCl$_2$, and 10 mM MgCl$_2$) were spread with 0.1 ml of the recipient *S. lividans* streptomycin$^r$ culture. Five μl of each donor Thio$^r$ culture was spotted on top of this lawn. After 7 days incubation at 35° C., the mating plates, together with plates of unmated donor and recipient cells were replicated to R2YE plates with 10 μg/ml thiostrepton and 100 μg/ml streptomycin to select exconjugants.

After 3 to 4 days incubation at 35° C. the selective plates contained thiostrepton$^r$ streptomycin$^r$ colonies which had arisen from transfer of pVE3 from donor cells into the streptomycin$^r$ recipient. Unmated control cultures gave rise to no doubly resistant colonies. This result indicated cointegrate plasmid pVE3 was self-transmissible.

E. Cloning of the tsr Gene Into pVE1

(1) Construction of recombinant plasmids.

In the following experiments a fragment containing only DNA encoding thiostrepton resistance (but no DNA of pBR322) was cloned into various restriction sites on pVE1. The experiment took advantage of the fact that the enzymes Bam HI, Bgl II and Bcl I, generate the same four base 5' extension, GATC, upon cleavage of the DNA. This made it possible to anneal and ligate fragments produced by each of these enzymes with fragments produced by any one of these enzymes.

Figure 6:
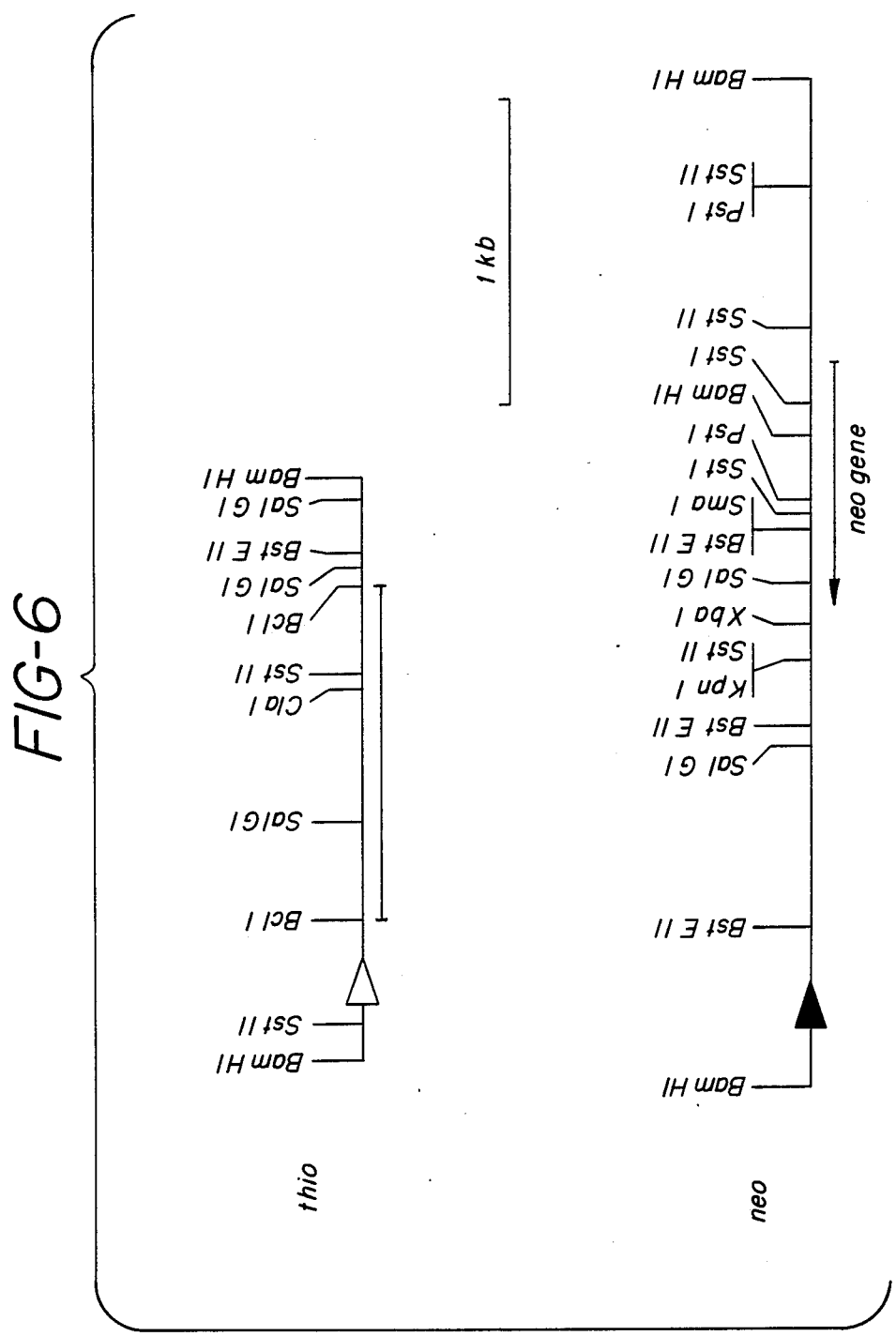
Figure 7:
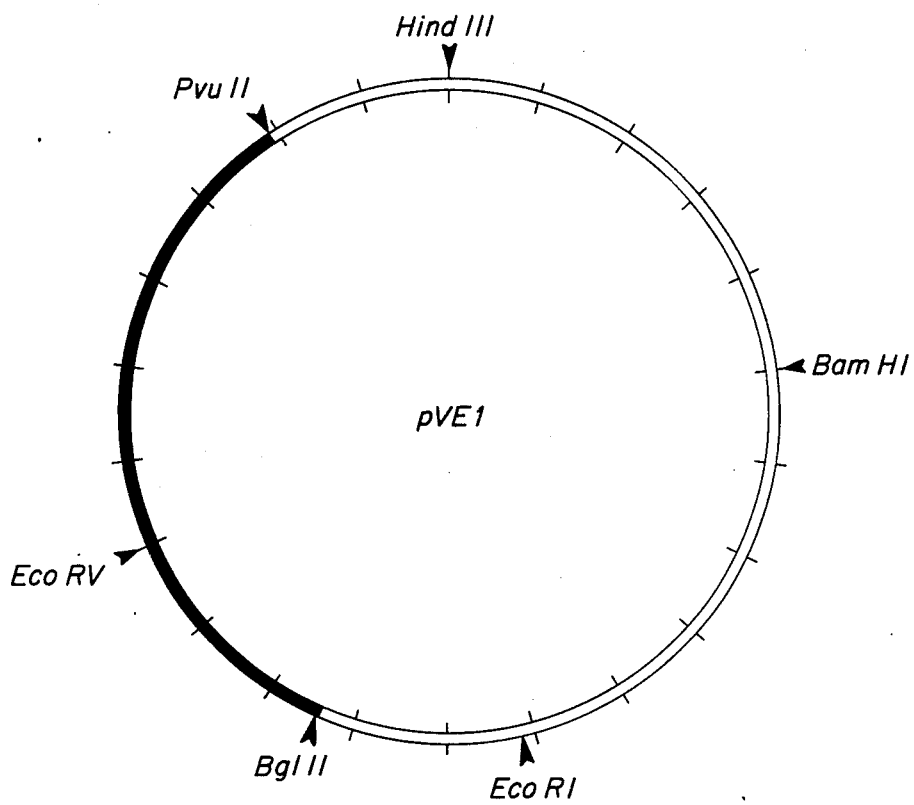
Figure 8:
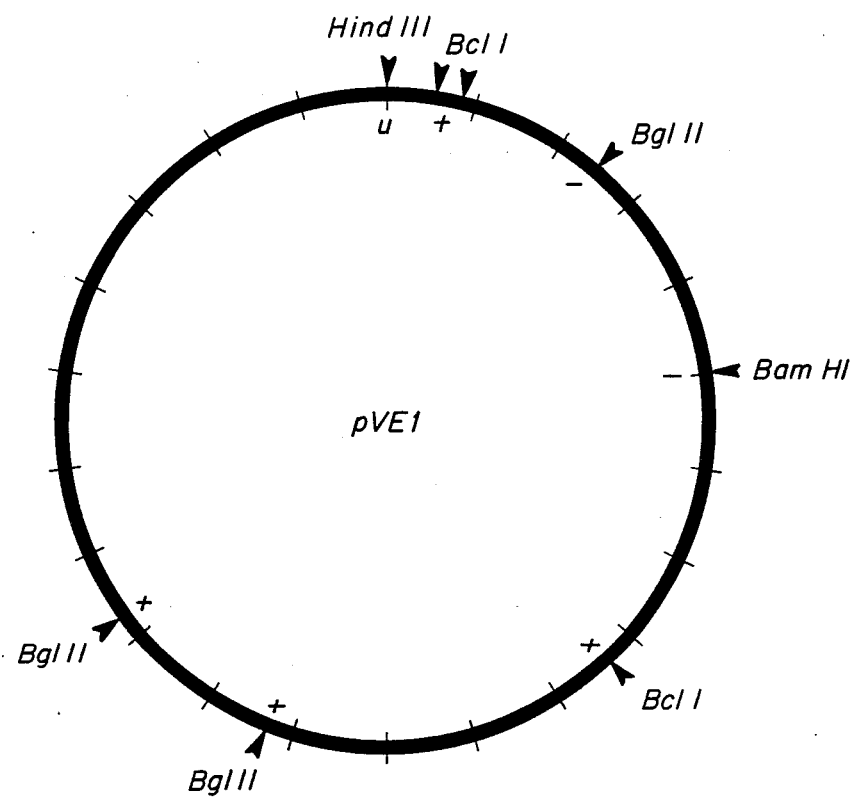

Plasmid pIJ39 contains a 1.9 kb Bam HI fragment with the tsr gene (see FIG. 6). Within this Bam HI fragment is a Bcl I 1.1 kb fragment which contains the intact tsr gene. Since Bcl I will not cleave *E. coli* methylated DNA due to the modification by the dam gene (Hattmen, S., Brooks, J. E. and Masurekar, M., 1978, *J. Mol. Biol.* 126: 267–380), a pIJ39 plasmid preparation was prepared from the dam$^-$ dcm$^-$ host GM272 (Marinus, M. G. and Konrad, E. B., 1976, *Mol. Gen. Genet.* 149: 273–277). The 1.1 kb Bcl I tsr fragment was inserted into the single Bam HI site, the three Bgl II sites and at least two of the four Bcl I sites of pVE1. In addition, the 1.9 kb Bam HI tsr fragment was cloned into pVE1. The details of these procedures follow.

pVE1 and pIJ39 were each separately cleaved with Bam HI. After inactivation of the restriction enzymes, 2μg, of linearized pVE1 was mixed with a 5 molar excess, 6 μg, of Bam HI cleaved pIJ39 and incubated with T4 DNA ligase overnight at 16° C. at a DNA concentration of 400 μg/ml in ligase buffer. One-half of this reaction mixture was used to transform S. lividans protoplasts. Thio$^r$ transformants were detected by the overlay method described above.

pVE1 contains three sites for Bgl II and four for Bcl I. It was desired to obtain independent recombinant plasmids with tsr in each of the possible sites. Therefore, conditions were determined in which incubation of restriction enzymes with pVE1 gave a DNA preparation only partially digested by the enzyme to obtain a significant number of plasmid molecules which had only been cleaved once by the enzyme. These linear molecules were the desired substrate for ligation. Such a population was presumably a mixture of pVE1 linearized at each possible site. pVE1 was incubated With Bgl II or Bcl I at a concentration of 0.1 to 1.0 unit of enzyme per μg of DNA. Samples were taken at 5, 10, 20, 40 and 80 min and analyzed by agarose gel electrophoresis to determine which conditions yielded predominantly linear molecules with a minimum amount of complete digestion products. These conditions had to be determined empirically for every batch of enzyme.

pVE1 partially cleaved with Bcl I and pVE1 partially cleaved with Bgl II were mixed and ligated with pIJ39 cleaved with Bcl I under conditions described for the other ligations and Thio$^r$ transformants were detected by the overlay method described above.

(2) Analysis of Recombinant Plasmids

Figure 2:
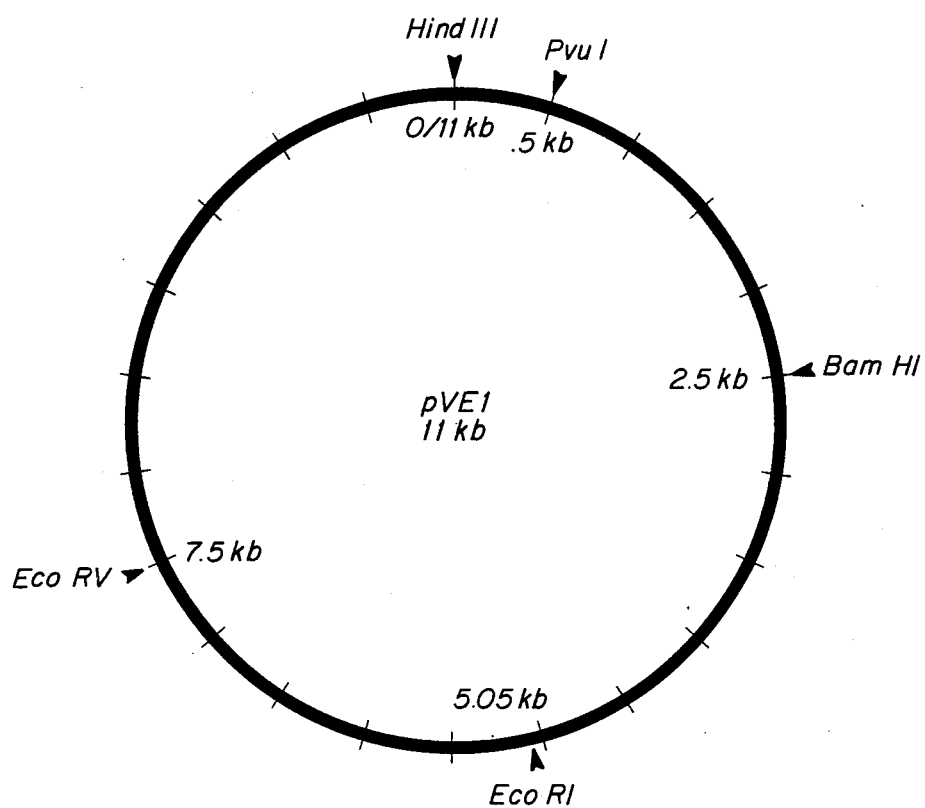

Thiostreptron$^r$ colonies were purified twice on R2YE-thio medium and then cultures of several from each ligation were analyzed by plasmid miniprep analysis. Restriction digests were performed to determine the site of the tsr insertion and the orientation of the Bam HI 1.9 kb tsr fragment or the Bcl I 1.1 kb tsr fragment. The restriction enzyme Cla I was used to determine the orientation and location of tsr in all ligation experiments. In the experiments which employed pVE1 partially cleaved with Bcl I the enzyme Pvu II was also used. These two enzymes were useful for these experiments because each cleaved pVE1 three times (see FIG. 1) and the tsr fragment once (see FIG. 6). The tsr Bam HI or Bcl I fragment each contained one asymmetrically located Cla I site and Pvu II site. This permitted assignment of an orientation to the tsr fragment. It was determined that the Pvu II site in tsr maps very near the Cla I site in the smaller gf the two Cla I Bcl I fragments from tsr. Digestion of recombinant Thio$^r$ plasmids with Cla I or Pvu II generated fragments whose sizes could be predicted from the restriction maps of pVE1 and tsr. Orientation 1 was defined as that orientation of either the Bam HI or the Bcl I tsr fragment in which there was encountered the Cla I or Pvu II site after the midpoint of the tsr fragment when moving clockwise around the recombinant plasmid as drawn in FIG. 2. Orientation 2 was the reverse of this orientation.

The following recombinant plasmids were identified from analysis of Cla I and Pvu II restriction patterns obtained from digestion of plasmid miniprep DNA. pVE9 and pVE11 contained the 1.9 kb Bam HI tsr fragment in the Bam HI site of pVE1 in orientations 1 and 2, respectively. pVE13 and pVE17 contained the 1.1 kb Bcl I tsr fragment in the Bam HI site in orientations 1 and 2, respectively. pVE19 and pVE21 contained the Bcl I tsr fragment in the Bgl II site at 6.15 kb in orientations 2 and 1, respectively. pVE23 contains the 1.1 kb Bcl I tsr fragment in the Bgl II site at position 7.15 kb. pVE24 and pVE26 contained this tsr fragment in the Bgl II 1.5 kb site in orientations 2 and 1, respectively. pVE33 and pVE35 contained the 1.1 kb Bcl I tsr fragment in the Bcl I site at 0.33 or 0.4 kb on pVE1 in orientations 2 and 1, respectively. However, it has not been determined in which of these two sites the insertions are located. pVE37 and pVE39 contained this fragment in the Bcl I 4.3 kb site in orientations 2 and 1, respectively.

Two recombinant plasmids which have deletions within pVE1 DNA were also obtained. The extent of the deletions was defined by restriction analysis employing enzymes shown in FIG. 1. pVE30 contained the 1.1 kb Bcl I tsr fragment in orientation 2 at the Bgl II 6.15 kb site accompanied by a deletion of 1.0 kb between the two Bgl II sites at 6.15 and 7.15 kb. As a result, pVE30 now had only a single Bgl II site, that at 1.5 kb. pVE28 contained the 1.1 kb Bcl I tsr fragment in orientation 2 at the Bgl II 6.15 kb site. This plasmid was only 5.1 kb in size due to a deletion of approximately 7 kb. The deletion began near, but did not remove, the Pvu II site at 10 kb, continued through the 0/11 kb site and removed pVE1 DNA approximately to the Bgl II kb site where tsr was inserted.

F. Determination of transmissibility of recombinant plasmids

Matings were performed with strains of *S. lividans* containing each of the recombinant plasmids to determine which sites of insertion were essential and nonessential for self-transmissibility of pVE1. Matings to a streptomycin$^r$ derivative of *S. lividans* were performed as described in mating experiments with the cointegrate plasmid pVE3. Matings were performed on R2YE plates which were then replicated to R2YE medium containing thiostrepton and streptomycin.

The four plasmids which contained insertions in the Bam HI site of pVE1 (pVE9, 11, 13 and 17) were not self-transmissible. pVE24 and pVE26 which contained tsr in the Bgl II 1.5 kb site, which was about 1.0 kb away from the Bam HI site, were also not self-transmissible. pVE28, the plasmid with the large 7 kb deletion, also failed to transfer Thio$^r$. All other recombinant plasmids were self-transmissible (Tra ). This included plasmids with insertions in either the Bgl II 6.15 or 7.15 kb sites as well as the plasmid which contained a deletion of the DNA between these two sites, pVE30. The four plasmids which had insertions in the Bcl I sites at 0.33 or 0.4 and 4.3 kb were all Tra$^+$.

G. Transformation of pVE1 Derivatives into *S. avermitilis*.

To determine whether pVE1 was a useful cloning vector for *S. avermitilis*, protoplasts of *S. avermitilis* MA4990 were transformed with plasmid DNA of pVE17 (pVE1 with 1.1 kb Bcl I tsr in the Bam HI site) and pVE28 (the plasmid with the 7 kb deletion). Protoplasts were prepared and transformed with plasmid DNA as described above. Thio$^r$ transformants were detected by the method of overlaying regeneration plates with soft agar containing thiostrepton. Both pVE17 and pVE28 transformations yielded thiostrepton$^r$ colonies of *S. avermitilis*. Ten colonies from each transformation were purified and analyzed by plasmid miniprep analysis. Restriction analysis indicated all strains contained at high copy number the intact pVE17 and pVE28 used in transformation. This experiment indicated that derivatives of pVE1 can be successfully used as cloning vectors in *S. avermitilis*.

Two detailed examples of how pVE1 replicons may be used are described below.

EXAMPLE 2

Cloning of Avermectin Genes pVE17 and pVE28 were successfully introduced into *S. avermitilis* and are, therefore, suitable cloning vectors. Any related pVE1 replicon might also function for this purpose. pVE17 is partially digested with Bcl I or Bgl II. Similarly pVE28 is linearized with Bgl II. *S. avermitilis* chromosomal DNA is partially digested with Sau3A. These enzymes generate the same 5' four base extension. *S. avermitilis* chromosomal fragments in the range of 3 to 10 kb are extracted after separation by agarose gel electrophoresis. These fragments are ligated with the cleaved plasmid DNA. The ligation mixture is used to transform a mutant of *S. avermitilis* blocked in the synthesis of avermectin to thiostrepton$^r$. Until a simple overlay is developed to screen for the production of avermectin, it is necessary to screen small cultures from thior colonies by high pressure liquid chromotography in order to identify those colonies containing the wild-type complementing gene on the recombinant plasmid which is capable of avermectin production.

EXAMPLE 3

Cloning Hepatitis B Surface Antigen Into streptomyces

Hepatitis B surface antigen can be cloned into *S. lividans* by insertion of the bulk of the C-terminal portion of the hepatitis B surface antigen gene into a gene expressed in *S. lividans*. If the surface antigen insert is in the correct orientation and translation or reading frame, a fusion protein having the antigenic properties of the hepatitis B surface antigen will be produced. (Edman, J. C., Hallewell, R. H., Valenzuela, P., Goodman, H. M. and Rutter, W. J., 1981, "Synthesis of hepatitis B surface and core antigens in *E. coli*," *Nature,* 291: 503–506). In the present example, the hepatitis B surface antigen is inserted into a gene conferring resistance to neomycin.

The aph gene conferring Neo$^r$ (see FIG. 6) is obtained by cleavage of pIJ2 DNA by Sst II. This 1.0 kb fragment is purified by agarose gel electrophoresis. The vector DNA (a pVE1 derivative with the Bcl I tsr fragment inserted in the single Bam HI site of pVE1 such as pVE13 or pVE17) is partially digested with Sst II. pVE1 has several Sst II sites so that partial digestion is necessary in order to obtain predominantly linear molecules. Cleaved vector DNA is ligated with a 1.0 kb aph fragment and used to transform *S. lividans* to Thio$^r$ Neo$^r$.

DNA of the Neo$^r$ Thio$^r$ plasmid is cleaved with Bam HI. The vector has a single Bam HI site which is located near the middle of the gene coding for resistance to neomycin. The vector is tailed with approximately 10 to 15 deoxyguanosine nucleotide residues by terminal deoxynucletidyl transferase. Cloned hepatitis B viral DNA is digested with Hinc II and a 744-base pair fragment containing part of the hepatitis B surface antigen (the 22 amino termial amino acids are missing) is isolated by polyacrylamide gel electrophoresis (Edman, J. c. et al., 1981, supra). This fragment is tailed with approximately 10 to 15 deoxycytidine nucleotide residues. The fragment is then hybridized with the tailed vector, and the mixture used to transform *S. lividans* protoplasts to Thio$^r$ and screened for neomycin sensitivity caused by insertion into the aph gene. Plasmid miniprep DNA from these strains is examined by restriction analysis to identify plasmids with insertion of the hepatitis B surface antigen fragment. These strains are examined for the production of the expected neomycin phosphotransferase-hepatitis B surface antigen fusion protein.

What is claimed is:

1. An isolated vector consisting essentially of pVE1 plasmid.

2. An isolated vector, pVE1 plasmid, comprising pVE1 DNA, or a deletion derivative vector thereof, and inserted foreign DNA.

3. A method for preparing a vector according to claim 2 comprising the separate steps of: cleaving the DNA of pVE1 plasmid vector; optionally deleting native DNA from said cleaved pVE1 plasmid vector; adding foreign DNA to said cleaved or cleaved/DNA deleted vector and ligating said foreign DNA into said cleaved or cleaved/DNA deleted vector, said steps being carried out once or successively, solely to the exclusion of the other, or together in any order, followed by a step of recovering said vector according to claim 2.

4. An isolated vector consisting essentially of a plasmid selected from the group consisting of pVE3, pVE9, pVE11, pVE13, pVE17, pVE19, pVE21, pVE23, pVE24, pVE26, pvE28, pVE30, pVE33, pVE35, pVE37, and pVE39.

5. An isolated vector consisting essentially of a plasmid selected from the group consisting of pVE3, pVE9, pVE1 , pVE13, pVE17, pVE19, pVE21, pVE23, pVE24, pVE26,pVE28, pVE30, pVE33, pVE35, pVE37 and pVE39, into which additional foreign DNA has been recombined.

6. A biologically pure culture of a microorganism containing a vector consisting essentially of a plasmid selected from the group consisting of pVE3, pVE9, pVE11, pVE13, pVE17, pVE19, pVE21, pVE23, pVE24, pVE26, pVE28, pVE30, pVE33, pVE35, pVE37 and pVE39, wherein said microorganism is one which can act as a host for said vector.

7. A biologically pure culture of a microorganism containing a vector consisting essentially of a plasmid selected from the group consisting of pVE3, pVE9, pVE11, pVE13, pVE17, pVE19, pVE21, pVE23, pVE24, pVE26, pVE28, pVE30, pVE33, pVE35, pVE37 and pVE39, wherein the microorganism is a Streptomyces species.

8. A biologically pure culture of a microorganism according to claim 7 wherein the microorganism is selected from the group consisting of *Streptomyces cattleya, Streptomyces avermitilis, Streptomyces venezuelae*, and *Streptomyces lividans*.

9. A biologically pure culture of a microorganism containing a vector consisting essentially of a plasmid selected from the group consisting of pVE3, pVE9, pVE11, pVE13, pVE17, pVE19, pVE21, pVE23, pVE24, pVE26, pVE28, pVE30, pVE33, pVE35, pVE37 and pVE39, wherein said microorganism is one which can act as a host for said vector.

10. A biologically pure culture of a microorganism according to claim 9 wherein the microorganism is a Streptomyces species.

11. A method according to claim 3 for the addition of foreign DNA to said vector which comprises cleaving the DNA of said vector and incorporating said additional foreign DNA.

12. A method according to claim 3 for the deletion of DNA from said isolated vector which comprises cleaving the DNA of said vector.

13. A method according to claim 11 for the addition of foreign DNA to said vector which comprises treating said vector with one or more restriction endonucleases in order to cleave the DNA thereof, followed by ligating said foreign DNA to said vector.

14. A method according to claim 13 wherein the restriction endonuclease is selected from the group consisting of Hind III, Eco RI, Eco RV, Bam HI, Pvu I, Bcl I, Bgl II, Cla I, Pst I, Sph I, Pvu II, Stu I, Not I, and Nru I.

15. A method for preparing a derivative of an isolated vector consisting essentially of a member selected from the group conssiting of pVE3, pVE9, pVE11, pVE13, pvE17, pVE19, pVE21, pVE23, pVE24, pVE26, pVE28, pVE30, pVE33, pVE35, pVE37, and pVE39, comprising the separate steps of adding foreign DNA to said vector and deleting DNA from said vector, said steps being carried out once or successively, solely to the exclusion of the other, or together in any order, followed by a step of recovering said derivative.

16. A method according to claim 15 for the addition of DNA to said vector which comprises cleaving the DNA of said vector and incorporating said additional foreign DNA.

17. A method according to claim 15 for the deletion of DNA from said isolated vector which comprises cleaving the DNA of said vector.

18. A method according to claim 17 for the addition of foreign DNA to said vector which comprises treating said vector with one or more restriction endonucleases in order to cleave the DNA thereof, followed by ligating said foreign DNA to said vector.

19. A method according to claim 18 wherein the restriction endonuclease is selected from the group consisting of Hind III, Eco RI, Eco RV, Bam HI, Pvu I, Bcl I, Bgl II, Cla I, Pst I, Sph I, Pvu II, Stu I, Not I, and Nru I.

20. An isolated vector prepared by the method of claim 15.

21. A biologically pure culture of a microorganism containing a vector according to claim 20 wherein said microorganism is one which can act as a host for said vector.

22. A biologically pure culture of a microorganism containing a vector according to claim 21 wherein the microorganism is a Streptomyces species.

23. A biologically pure culture of a microorganism containing a vector, pVE1 plasmid, said plasmid comprising pVE1 DNA, or a deletion or derivative vector thereof, and inserted foreign DNA wherein said microorganism is one which can act as a host for said vector.

24. A biologically pure culture of a microorganism according to claim 23 wherein the microorganism is a Streptomyces species, and wherein said microorganism is one which can act as a host for said vector.

25. A biologically pure culture of a microorgansim containing a vector according to claim 23 wherein the microorganism is selected from the group consisting of *Streptomyces cattleya, Streptomyces avermitilis,* and *Streptomyces lividans.*

* * * * *